(12) United States Patent
Weidmann et al.

(10) Patent No.: US 9,244,006 B2
(45) Date of Patent: Jan. 26, 2016

(54) DETECTING SPECIES IN A DILUTE MEDIUM

(75) Inventors: Damien Weidmann, Reading (GB); Gerard Wysocki, Princeton, NJ (US)

(73) Assignee: The Science and Technology Facilities Council, Didcot (GB)

( * ) Notice: Subject to any disclaimer, the term of this patent is extended or adjusted under 35 U.S.C. 154(b) by 565 days.

(21) Appl. No.: 13/502,039

(22) PCT Filed: Nov. 12, 2010

(86) PCT No.: PCT/GB2010/002095
§ 371 (c)(1),
(2), (4) Date: Jul. 17, 2012

(87) PCT Pub. No.: WO2011/058330
PCT Pub. Date: May 19, 2011

(65) Prior Publication Data
US 2012/0274929 A1   Nov. 1, 2012

(30) Foreign Application Priority Data
Nov. 12, 2009   (GB) .................................. 0919854.0

(51) Int. Cl.
*G01B 9/02*       (2006.01)
*G01N 21/45*      (2006.01)

(52) U.S. Cl.
CPC ...................................... *G01N 21/45* (2013.01)

(58) Field of Classification Search
CPC ................ G01N 21/45; G01N 21/455; G01N 2021/451; G01B 9/02003; G01B 9/02007
USPC .......................................................... 356/484
See application file for complete search history.

(56) References Cited

U.S. PATENT DOCUMENTS

| 4,847,512 A | 7/1989 | Seta |
| 6,327,039 B1 | 12/2001 | de Groot et al. |

(Continued)

FOREIGN PATENT DOCUMENTS

| EP | 0 920 599 A1 | 6/1999 |
| EP | 1 058 813 A1 | 12/2000 |

(Continued)

OTHER PUBLICATIONS

Moschella et al., "Resonant, heterodyne laser interferometer for state density measurements in atoms and ions", Review of Scientific Instruments, vol. 77, No. 093108-1, 2006.

(Continued)

*Primary Examiner* — Tarifur Chowdhury
*Assistant Examiner* — Jonathon Cook
(74) *Attorney, Agent, or Firm* — Birch, Stewart, Kolasch & Birch, LLP

(57) ABSTRACT

Method and apparatus for detecting a species in a dilute medium, the species having a spectral feature, the apparatus comprising: a beam source arranged to generate a first laser beam and a second laser beam coherent with each other, and having a matching chirp pattern. Beam guide arranged to pass at least the first laser beam through the dilute medium; a beam mixer arranged to mix the first and the second laser beams to form a mixed beam. Detector arranged to detect, during the chirp pattern, the mixed beam and to measure changes in the mixed beam caused by refractive index variations in the dilute medium across a spectral feature. Output providing a signal that changes in response to the measured changes.

26 Claims, 8 Drawing Sheets

(56) References Cited

U.S. PATENT DOCUMENTS

| | | | |
|---|---|---|---|
| 8,334,980 B2* | 12/2012 | So et al. | 356/432 |
| 2005/0041253 A1* | 2/2005 | Pearson | 356/484 |
| 2006/0012797 A1* | 1/2006 | Chang et al. | 356/484 |

FOREIGN PATENT DOCUMENTS

| | | |
|---|---|---|
| JP | 11-14544 A | 1/1999 |
| JP | 2008134076 A | 6/2006 |
| WO | WO 98/08047 A1 | 2/1998 |

OTHER PUBLICATIONS

Schwarze et al., "Method for obtaining gas concentration with a phase-based metrology system", Applied Optics, XP002621558, vol. 37, No. 18, pp. 3942-3947, Jun. 20, 1998.

Taslakov et al., "Open path atmospheric spectroscopy using room temperature operated pulsed quantum cascade laser", Spectrochimica Acta. Part A, XP025176687, vol. 63, No. 5, pp. 1002-1008, Apr. 1, 2006.

AA Molecular dispersion spectroscopy for chemical sensing using chirped mid-infrared quantum cascade laster, G. Wysocki and D. Weidmann, 2010 OSA, Dec. 6, 2010/vol. 18, No. 25/Optics Express 26123.

A new method for measuring relative oscillator strengths using CW dye laser, M. Crance et al., J. Phys. B: Atom, Molec. Phys., vol. 8, No. 15, 1975.

Anomale Dispersion im Natriumdampf; von D. Roschdestwensky, Hierzu Taf. II, Figg. 1-2, Taf. III, Taf. IV, Figg. 1-3; Taf. V, Figg. 1-3.

Application of dispersion techniques to molecular band instensity measurements; I. Principles of 'fringe shitf' and 'fringe slope' band analysis procedures, V. Hasson et al., J. PHys. B: Atom. Molec. Phys., vol. 5, Jun. 1972.

Difference frequency generation laser based spectrometers, D. Richter, et al., Laser & Photon. Rev. 3, No. 4, 343-354 (2009).

Measurement of oscillator strength by tunable laster interferometry, A. Duval and A. McIntosh, J. Phys. D: Appl. Phys., 13 (1980) 1617-23.

Measurement of the refractive index dispersion around an absorbing line, S. Marchetti & R. Simili, Optics Communications 249 (2005) 37-41.

Measurements of the Anomalous Dispersion of HF in Absorption, R. Gross et al., IEEE Journal of Quantum Electronics, vol. QE-16 No. 7, Jul. 1980.

OH Concentration Measurements by Resonant Holographic Interferometry and Compasion with Direct Numerical Simulations, A. Tzannis et al., Flow, Turbulence and Comnustion 64: 183-196, 2000.

Possibility of Intraresonator Double-Beam Spectrointerferometry of Phase Objects Using a Dye Laser, O. Denchev et al., UDS 535.542.3, Translated from Zhurnal Prikladnoi Spektroskopii, vol. 36, No. 3, pp. 377-383, Mar. 1982.

Precision measurements of sodium-sodium and sodium-noble gas molecular absorption, M. Shurgalin et al., Meas. Sci. Technol. 11 (2000).

The Anomalous Dispersion of Sodium Vapour, R. Wood, Proc. R. Soc. Lond. 1901 69, 157-171, published Jan. 1, 1901.

Ultra-sensitive ambient ammonia detection using $CO_2$-loaser-based photoacoustic spectroscopy, M. Pushkarsky et al, Appl. Phys. B 77, 381-385 (2003).

* cited by examiner single line 1912.8 recorded on the bump
baseline corrected

DETECTING SPECIES IN A DILUTE MEDIUM

This invention was made with government support under Grant No. EEC-0540832 awarded by the National Science Foundation. The government has certain rights in this invention.

FIELD OF THE INVENTION

The present invention relates to methods and apparatus for detecting a species in dilute medium and in particular to detecting a molecular species in a gas sample or an atmosphere.

BACKGROUND OF THE INVENTION

Absorption spectroscopy and fluorescence spectroscopy are commonly used to detect the presence of particular chemical species in a range of samples, especially dilute media such as gases. Absorption of narrow band laser light by a particular molecular transition may be detected by a reduction in detected intensity or amplitude especially in the ultraviolet or visible spectrum. Absorption of broad band light may be due to one or a plurality of molecular transitions and may also be detected by spectroscopic analysis of the light. Similarly, fluorescence arising from excited molecular states may also be detected.

However, such techniques typically rely on amplitude detection and so are susceptible to scintillation and laser noise.

"Resonant, heterodyne-laser-interferometer for state density measurements in atoms and ions", Review of Scientific instruments 77, 093108 (2006), J. J. Moschella, et al., describes a resonant, two-wavelength heterodyne interferometer for measuring the population density of plasmas. Two separate lasers are used and an acousto-optical modulator splits the beams. However, this system is not particularly suitable for dilute species where the signal may be swamped by noise and other factors.

Therefore, there are required methods and apparatus for detecting dilute species that overcome these problems.

SUMMARY OF THE INVENTION

The refractive index of a medium changes with wavelength. However, as the illuminating wavelength approaches and passes through an absorption, electronic, vibration or other spectral feature of the medium, this change in refractive index may be particularly abrupt or dramatic, which generally returns to a baseline or more gradually changing refractive index, as the illuminating wavelength moves away from the spectral feature. Therefore, measurements of the species in a dilute medium may be inferred from measurements of the refractive index change. For example, the concentration of the species in the dilute medium may be calculated from refractive index change measurements, especially where the spectral feature of the species does not coincide with a spectral feature of the dilute medium.

In accordance with a first aspect of the present invention there is provided a method of detecting a species in a dilute medium comprising: providing a first laser beam and a second laser beam coherent with each other, and having a matching chirp pattern; passing at least the first laser beam through the dilute medium, whilst the chirp pattern of the first laser beam crosses at least a part of a spectral feature of the species; mixing the first and the second laser beams to form a mixed beam; detecting the mixed beam to form an output signal during the chirp pattern; processing the output signal to measure changes in the mixed beam caused by refractive index variations in the dilute medium across the spectral feature; and determining a measure of the species from the changes in the measured properties. Chirping the laser improves detectability. Therefore, both beams may be coherent. As the rate of change of frequency of the laser increases, so does the signal-to-noise. The spectral feature may be a spectral absorption feature, for instance.

Optionally, the first and second laser beams may both pass through the dilute medium and an optical frequency shift may be applied to the second laser beam before mixing the first and the second laser beams. Therefore, both beams may experience different effective path lengths as a spectral feature is encountered by one beam. The optical frequency shift may be applied to the second laser beam at the same time as splitting a single beam to form the first and second laser beams or as a separate procedure.

Optionally, the chirp pattern of the second laser beam may not cross the spectral feature of the species.

Optionally, the measured changes in the mixed beam include changes in the optical frequency difference between the first and second laser beams. Changes in wavelength and/or phase may also be measured.

Preferably, the optical frequency difference may be between 1 MHz and 1 GHz. This may depend on the linewidth of the spectral feature.

Optionally, the detecting step may further comprise detecting a beat signal in the mixed beam due to the optical frequency difference.

Advantageously, the changes in the mixed beam caused by the refractive index variations may include changes in phase and the processing step may further comprise measuring the changes in phase of the mixed beam.

Preferably, the detecting step may further comprise detecting the frequency changes in the beat signal. This provides a convenient measure that may change with refractive index.

Optionally, processing the output signal may further comprise measuring a change in optical path difference between the first laser beam and the second laser beam caused by refractive index variations in the dilute medium across the spectral feature.

Preferably, the change in optical path difference may be measured by comparing phase properties of the mixed beam.

Optionally, the first and second laser beams are generated using a quantum cascade laser. Other beams sources or lasers may be used that may be coherently chirped.

Preferably, during the chirp pattern, the first and second laser beams change frequency at a rate of at least 100 Hz/ns, and more preferably at least 100 KHz/ns.

Preferably, each chirp pattern may cross at least a part of the spectral feature in less than 10 msec, and more preferably in less than 10 μs. The faster this occurs the higher the signal-to-noise.

Optionally, the spectral feature may be selected from the group consisting of: electronic absorption, molecular transition, rotational transition, ro-vibrational transition, band gap and vibrational band. Other spectral features may be used.

In accordance with a second aspect of the present invention, there is provided a use of changes in refractive index of a gas sample across at least part of a spectral feature of a species in the gas sample to detect the species. The refractive index may be measured by passing a beam through the gas sample. The beam may be a laser and may be chirped.

In accordance with a third aspect of the present invention, there is provided apparatus for detecting a species in a dilute medium, the species having a spectral feature, the apparatus comprising: a beam source arranged to generate a first laser beam and a second laser beam coherent with each other, and having a matching chirp pattern; a beam guide arranged to pass at least the first laser beam through the dilute medium; a beam mixer arranged to mix the first and the second laser beams to form a mixed beam; a detector arranged to detect, during the chirp pattern, the mixed beam and to measure changes in the mixed beam caused by refractive index variations in the dilute medium across a spectral feature; and an output providing a signal that changes in response to the measured changes.

Optionally, the beam guide may be further arranged to guide the first and second laser beams through the dilute medium, the apparatus further comprising an optical frequency shifter arranged to apply an optical frequency shift to the second laser beam before the beam mixer.

Optionally, the beam guide may be further arranged to guide the first and second laser beams through an open atmosphere. This open path arrangement allows atmospheric sensing such as pollution and trace chemical monitoring. A retro-reflector and/or the backscattering from particulates in the atmosphere and telescope arrangement may be used to increase the beam length, for example.

Preferably, the optical frequency shifter may be an acousto-optic modulator, AOM. An AOM may both split a single beam into separate beams and shift the wavelength of one beam relative to another. The AOM may form a $0^{th}$ and $1^{st}$ order beam such that the $0^{th}$ beam does not experience any frequency or wavelength shift. Either of these beams may be the first or second laser beam.

Optionally, the beam source is a quantum cascade laser, QCL. Other beams sources may be used, including for example, mid-infrared optical parametric oscillators (OPOs) that may use two laser components separated by a few hundred MHz.

Preferably, the beam source may further comprise a laser driver arranged to provide a driving signal to produce the chirp pattern. The chirp mechanism or means may be incorporated in the beam source or laser or be an external component or components.

Optionally, the apparatus may further comprise an adjustable delay line for changing the relative optical path lengths of the first and second laser beams. This may be used to tune the apparatus or cancel out unwanted optical effects.

Optionally, the detector may be an optical heterodyne detector. This may be used especially with an AOM that introduces a sum and difference frequency to the beam.

Preferably, the detector may further comprise an amplitude demodulator and/or a frequency demodulator. This may be in the form of a spectrum analyser or similar device.

Preferably, the apparatus may further comprise a cell for containing the dilute medium.

Optionally, the apparatus may further comprise a second cell for containing a reference sample, wherein the beam guide is further arranged to guide the second laser beam through the second cell. Therefore, comparison measurements may be made.

It should be noted that any feature described above may be used with any particular aspect or embodiment of the invention.

BRIEF DESCRIPTION OF THE FIGURES

The present invention may be put into practice in a number of ways and embodiments will now be described by way of example only and with reference to the accompanying drawings, in which.

It should be noted that the figures are illustrated for simplicity and are not necessarily drawn to scale.

DETAILED DESCRIPTION OF THE PREFERRED EMBODIMENTS

Quantum cascade lasers (QCL) have been used to measure absorption signal of molecular gases in a particular fingerprint region. These implementations of QCL-based tunable laser absorption spectroscopy are primarily based on trace gas detection and/or real time gas monitoring via laser intensity changes. The present invention instead uses a refractive index change to measure a species in a dilute medium and especially in gas or air.

Figure 1:
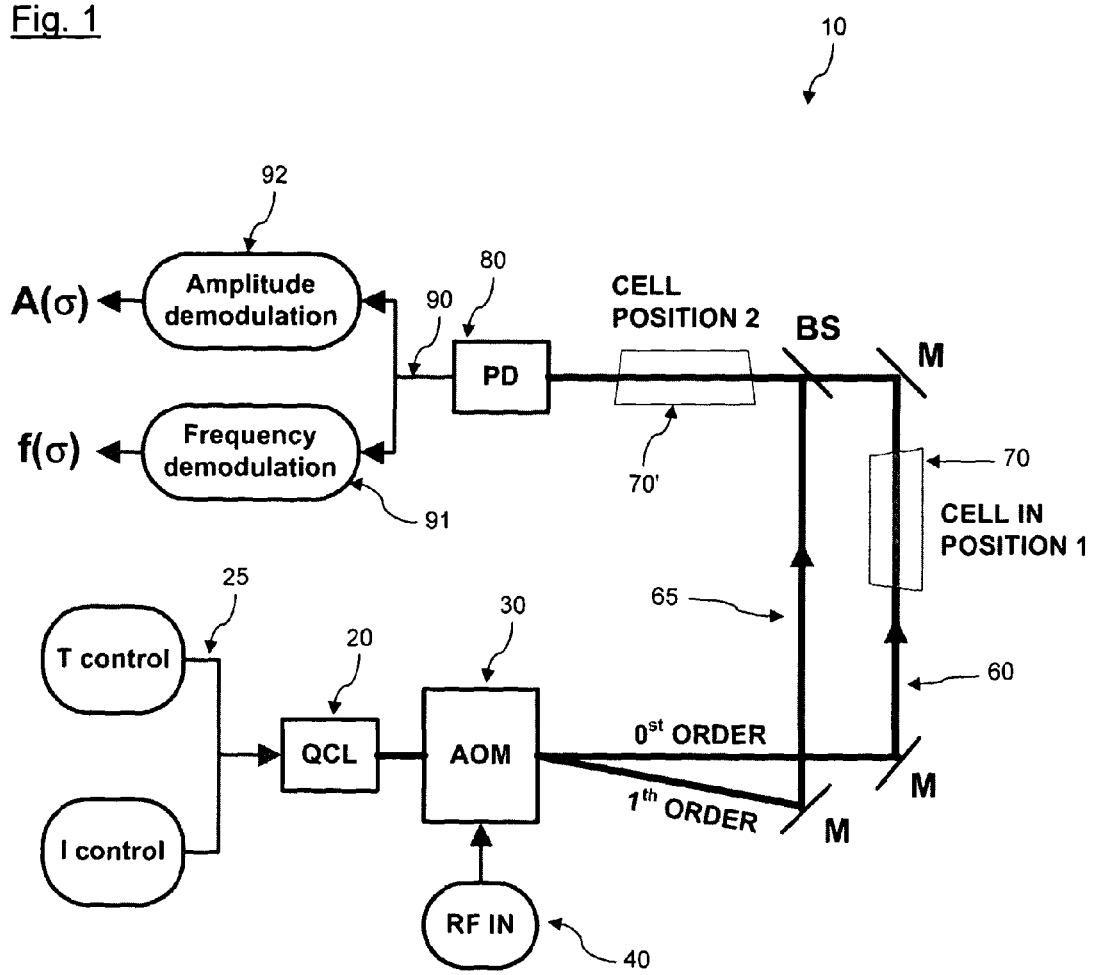
FIG. 1 shows a schematic diagram of an example system for detecting a species in a dilute medium held in a sample cell.

For particularly dilute mixtures, this change in refractive index may be very small and subject to higher levels of noise. FIG. 1 shows a schematic diagram of a system 10 for detecting species in a dilute medium that uses the change in refractive index phenomenon described above. QCL 20 is tuneable and may be chirped (i.e. wavelength-varied over a period) by controls 25. The laser beam from the QCL is split into two laser beams using an acousto-optic modulator (AOM) 30 driven by a radio frequency (RF) supply 40. The first beam corresponds with a $0^{th}$ order beam from the AOM 30 and the second beam corresponds to a $1^{st}$ order beam from the AOM 30. Therefore, the first and second beams will be frequency shifted by the frequency of the RF supply 40. The span of the frequency shift in the chirping of the QCL 20 together with the frequency of the radio frequency (RF) supply 40 are chosen so that one of the beams will change wavelength to coincide at some point during its chirping pattern to coincide with a spectral feature of the species to be measured. In the example shown in FIG. 1, the $0^{th}$ order beam 60 will change wavelength to correspond with such a feature, whereas the $1^{st}$ order beam 65 will not. Alternatively, the apparatus may operate with the $1^{st}$ order beam 65 (and not the $0^{th}$) corresponding with a spectral feature during its chirp pattern.

An arrangement of mirrors M and a beam splitter BS recombines the $0^{th}$ and $1^{st}$ order beams to provide a mixed beam detectable by photo detector 80. A sample cell 70 is shown in FIG. 1 having two alternative positions. With the sample cell 70 in position 1, only the $0^{th}$ order beam 60 passes through the sample cell 70 containing a species and dilute medium. With the sample cell 70' in position 2, both beams pass through the sample cell 70' after being recombined by the mirror M and beam splitter BS arrangement.

The $0^{th}$ order beam 60 and the $1^{st}$ order beam 65 have a wavelength difference determined by the frequency of the RF supply 40, as described above. Therefore, the recombined or mixed beams will interfere to provide a beat pattern detectable by photo detector 80. This beat pattern will also have the frequency of the RF supply 40. However, as the QCL 20 chirps and one of the beams passes through a frequency corresponding with a spectral feature of the species, the apparent path length of that beam will change. In other words, a delay will be applied to that beam as it passes through the sample cell 70 or 70' retarding or advancing that beam only, whereas the other beam that does not pass through the spectral feature, in terms of frequency or wavelength, will be less affected or unaffected by the spectral feature. This effect will change the beat pattern detected by the photo detector 80, which provides an output signal that may be demodulated by either or both a frequency demodulator 91 and an aptitude demodulator 92.

In one example, measurements may be taken of refractive index changes of a molecular gas medium or other species (for example NO diluted in $N_2$), while chirping a frequency of a 5.2 μm quantum cascade laser across two fundamental transitions of the species. Phase information of the electromagnetic field may be measured through frequency demodulation of the beating signal between the $0^{th}$ and $1^{st}$ orders laser beams generated by the AOM 30.

In this example, the refractive index change signal scales with the chirp rate. QCLs can exhibit very high frequency chirp rates (up to about 300 MHz/ns) which makes these lasers particularly attractive for the method.

As shown in FIG. 1, a single mode QCL 20 shines through the AOM 30. The $0^{th}$ and $1^{st}$ orders diffracted by the AOM 30 travel through two distinct optical arms of an interferometer of the apparatus and are recombined on the photo-detector or photodiode 80, whose photocurrent is frequency-demodulated. As indicated in FIG. 1, the sample cell containing the sample to analyze can be placed either in the so-called position 1 where only the $1^{st}$ order diffracted beam passes through, or in position 2, where both orders pass through the sample.

Respectively to the $0^{th}$ and the $1^{st}$ order beams, two complex electric fields arriving on the photodiode surface can be written:

$$E_1 = A_1 \exp[i(\omega_1 t - \phi_1)] \text{ and,} \qquad \text{(Equation 1)}$$

$$E_2 = A_2 \exp[i(\omega_2 t - \phi_2)], \qquad \text{(Equation 2)}$$

with A, ω, and φ respectively being the amplitude, the pulsation, and the phase of the fields. In addition, as the AOM 30 provides a frequency shift on the $1^{st}$ order beam 60, one has: $\omega_2 = \omega_1 + \Omega$, with Ω the AOM 30 excitation frequency. At the detector surface, $E_1$ and $E_2$ beat together, and providing that the beating frequency lies within the electrical bandwidth of the photo detector 80, the resulting photocurrent may be proportional to:

$$I_{ph} \propto A_1^2 + A_2^2 + 2A_1 A_2 \cos[(\omega_1 - \omega_2)t - (\phi_1 - \phi_2)]. \qquad \text{(Equation 3)}$$

Let φ(t) be the phase term of the beating signal.
Cell in Position 1

Figure 10:
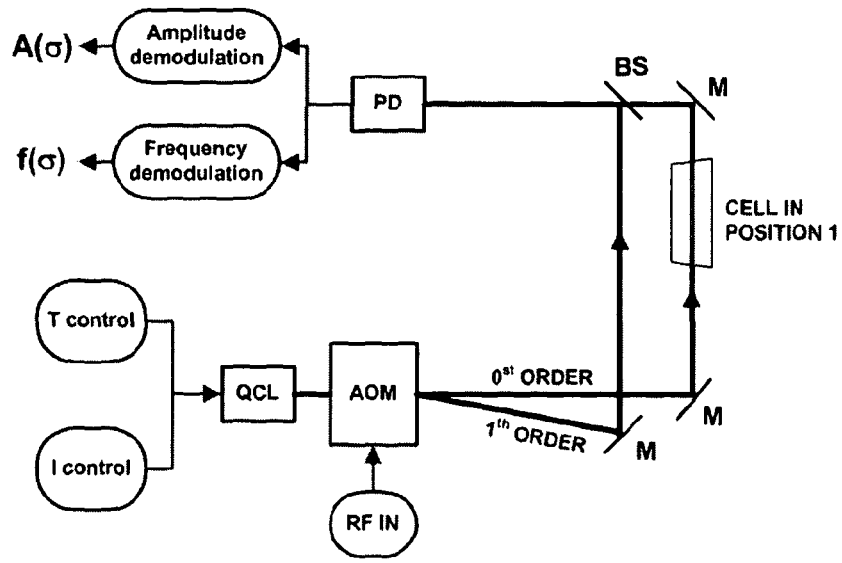
FIG. 10 shows a schematic diagram of an example system for detecting a species in a dilute medium held in a sample cell in a first position.

FIG. 10 shows a schematic diagram with the sample cell 70 in position 1. The sample cell 70 has a geometrical length of Lc and contains a dilute medium with a frequency dependant complex refractive index given by:

$$N(\omega) = n(\omega) + i \cdot \kappa(\omega). \qquad \text{(Equation 4)}$$

After propagation through the optical system, at the detector surface, the two fields as expressed in (Equation 1) and (Equation 2) become:

$$E_1 = A_1 \exp[-\kappa(\omega_1) k_1 Lc] \cdot \exp[i(\omega_1 t - (k_1(L+\Delta L) + n(\omega_1) k_1 Lc))] \qquad \text{(Equation 5)}$$

$$E_2 = A_2 \exp[i(\omega_2 t - k_2 L)]. \qquad \text{(Equation 6)}$$

L represents the optical length of the $1^{st}$ order diffracted beam 60, and ΔL accounts for the open air path difference between the $1^{st}$ and the $0^{th}$ orders, the length through the sample cell 70 being excluded. Further calculations yield the phase term of the beating signal to be:

$$\phi(t) = \Omega t + \frac{\omega_1}{c} \Delta L + n(\omega_1) \frac{\omega_1}{c} Lc + \frac{\Omega}{c} L \qquad \text{(Equation 6)}$$

In addition to the carrier frequency, the phase term contains information about the optical path difference between the two beams and hence the refractive index change occurring in the sample cell 70.

The instantaneous frequency may be given by $$2\pi \cdot f(t) = \frac{d\phi}{dt}.$$

After rearrangement, the demodulated frequency measured by the system may be:

$$2\pi \cdot f(t) = \frac{1}{c} \cdot \frac{d\omega}{dt} \cdot \left[\Delta L + Lc\left(n(\omega) + \omega \frac{dn}{d\omega}(\omega)\right)\right]. \qquad \text{(Equation 7)}$$

As $n(\omega_1) \cong 1$, (Equation 7) shows that the frequency demodulated signal may contain information of the first derivative of the real part of the complex refractive index. In addition, the importance of the laser frequency scan speed in the magnitude of the observed signal is noticeable. Where there is a linear laser frequency chirp then:

$$\frac{d\omega}{dt} \equiv \text{Constant} \equiv S, \qquad \text{(Equation 8)}$$

and the measured frequency becomes:

$$2\pi \cdot f(t) = \frac{1}{c} \cdot S \cdot (\Delta L + Lc) + \frac{1}{c} \cdot S \cdot Lc \cdot \omega \cdot \frac{dn}{d\omega} \qquad \text{(Equation 9)}$$

Under linear laser chirp conditions, the first term of (Equation 9) remains constant. This term can be zeroed through a substantially perfect optical arm balancing: $\Delta L = -Lc$. The second term contains the first derivative of the refractive index amplified by the laser frequency, and most importantly the laser chirp rate.
Cell in Position 2

Figure 11:
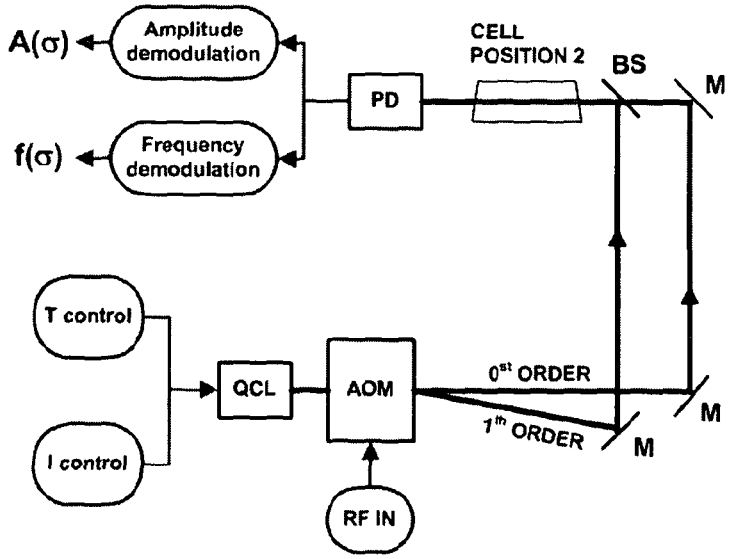
FIG. 11 shows a schematic diagram of an example system for detecting a species in a dilute medium held in a sample cell in a second position.

FIG. 11 shows a schematic diagram with the sample cell 70' in position 2. When the sample cell 70' is inserted in position 2, with both beams propagating through it, the two optical fields on the detector surface can be expressed as:

$$E_1 = A_1 \exp[-\kappa(\omega_1) k_1 L c] \cdot \exp[i(\omega_1 t - (k_1 L + n(\omega_1) k_1 L c))] \quad \text{(Equation 10)}$$

$$E_2 = A_2 \exp[-\kappa(\omega_2) k_2 L c] \cdot \exp[i(\omega_2 t - (k_2 (L + \Delta L) + n(\omega_2) k_2 L c))] \quad \text{(Equation 11)}$$

As $\omega \ll \omega_1$, and when typical linewidths of the spectral features under consideration are much greater than the AOM frequency from the RF input source 40, the following simplification can be made:

$$n(\omega_2) \approx n(\omega_1) + \Omega \frac{dn}{d\omega}(\omega_1) \quad \text{(Equation 12)}$$

Therefore, the beating signal phase term may be expressed as:

$$\phi(t) = \Omega t + \frac{\omega_1}{c} \Delta L + \Omega \frac{dn}{d\omega}(\omega_1) \frac{\omega_1}{c} Lc + n(\omega_1) \frac{\Omega}{c} Lc + \quad \text{(Equation 13)}$$
$$\frac{dn}{d\omega}(\omega_1) \frac{\Omega^2}{c} Lc + \frac{\Omega}{c}(L + \Delta L)$$

Typically, the first three terms of the phase are more than 5 orders of magnitude greater than the remaining terms. By keeping only those, after frequency demodulation, the signal may be approximated to:

$$2\pi \cdot f(t) = \frac{1}{c} \cdot \frac{d\omega}{dt} \cdot \left[ \Delta L + \Omega \cdot Lc \cdot \left( \frac{dn}{d\omega} + \omega \frac{d^2 n}{d\omega^2} \right) \right] \quad \text{(Equation 14)}$$

The first term in the round brackets may be neglected. If we consider a linear laser frequency chirp, then (Equation 14) becomes:

$$2\pi \cdot f(t) = \frac{1}{c} \cdot \Delta L \cdot S + \frac{1}{c} \cdot \Omega \cdot Lc \cdot S \cdot \omega \frac{d^2 n}{d\omega^2}. \quad \text{(Equation 15)}$$

This time, under the assumptions made for Equation 12, when the two optical arms are perfectly or substantially balanced, the frequency signal may provide the second derivative of the refractive index, further amplified by the AOM frequency. Once again, the signal scales with the laser frequency scan speed. When the AOM frequency is in the order of the typical linewidth of the transition under study, then Equation 12 is no longer valid.

Refractive Index Calculations

Kramers-Kronig relations may be used to compute the real part of the refractive index, knowing the absorption coefficient of the sample under examination. For a dilute medium, the Kramers-Kronig relations can be rewritten into a single equation relating the refractive index and the absorption coefficient of the medium:

$$n(\omega) = 1 + \frac{c}{\pi} \int_0^{+\infty} \frac{\alpha(\omega)}{\Omega^2 - \omega^2} d\Omega. \quad \text{(Equation 16)}$$

Using available data and an algorithm performing calculation of line-by-line absorption spectra, (Equation 16) may be used to compute the real part of the refractive index, which may be integrated into the model.

The optical setup is depicted schematically in FIG. 1. The laser source is a 5.2 µm distributed feedback (DFB) QCL 20 operating continuous wave at room temperature. QCL temperature and current are controlled (preferably precisely) and laser frequency modulation may be achieved through laser injection current modulation, for instance.

After collimation, the QCL beam goes through a germanium AOM 30 that can operate between 40 and 50 MHz, for example. The $0^{th}$ and the $1^{st}$ order beams may be separated by ~2.2° at 45 MHz. The two beams propagate separately in two optical arms. A beam splitter BS (e.g. calcium fluoride) recombines the two beams onto the photodetector 80 at room temperature. The photodetector output may be fed into a spectrum analyzer, (e.g. Tektronics), which performs frequency and amplitude demodulation of the detector signal 90.

The sample cell 70 may be 15 cm long and equipped with tilted calcium fluoride windows. A gas mixture composed of nitric oxide (NO), for instance, may be diluted in dry nitrogen to fill the sample cell 70. The NO mixing ratio used in this example is (0.98±0.11) % with a sample total pressure of (5±1) Torr. The v=0→v=1 fundamental band of NO is located at 5.3 µm. Therefore, this mid-infrared region of the spectrum is suitable to monitor the most intense ro-vibrational transitions of this particular example molecule. Given the tuning range of the DFB QCL 20, the rotational transitions given in table 1 have been targeted for experimental demonstration. Lines labeled 1 and 2 in the table may appear as a Λ-doublet, whereas the splitting of lines 3 and 4 may not be resolved due to collisional broadening, and may appear as a single transition. The QCL 20 may be operated at 115.5 mA and −15° C. to target the doublet (transitions 1 & 2), and at 113 mA, −20° C. to target the single line (non-resolved transitions 3 & 4), for example.

TABLE 1

Spectroscopic characteristics of the NO transitions used in the experiment. Data are from the HITRAN database.

| Line | Frequency cm$^{-1}$ | Band | Subband | Rotational Transition |
|---|---|---|---|---|
| 1 | 1912.0716 | v = 0 → v = 1 | $^2\Pi_{1/2}$ | R(10.5e) |
| 2 | 1912.0816 | v = 0 → v = 1 | $^2\Pi_{1/2}$ | R(10.5f) |
| 3 | 1912.7939 | v = 0 → v = 1 | $^2\Pi_{3/2}$ | R(10.5e) |
| 4 | 1912.7955 | v = 0 → v = 1 | $^2\Pi_{3/2}$ | R(10.5f) |

Measurement Close to Linear Laser Frequency Chirp

With the sample cell 70 in position 1 (only one beam through the cell) and the QCL 20 adjusted to target the doublet, a triangular current modulation (8 mA peak to peak) may be applied to the laser to approach the ideal case of a laser frequency linear chirp. The period of the modulating signal may be changed to modify the laser tuning speed. The graphs in FIGS. 4A-4D show the amplitude and frequency signals recorded for four example scan speeds: 0.27, 0.53, 0.8, and 1.6 A/s, corresponding to 174 Hz/ns, 347 Hz/ns, 521 Hz/ns, and 1043 Hz/ns, respectively. Whilst the absorption signal remains substantially unaffected (except the abscissa shrinkage due to higher tuning speed, in accordance with (Equation 9), the constant frequency offset and the signal amplitude may be shown to scale with the laser tuning speed in this example.

Figure 4:
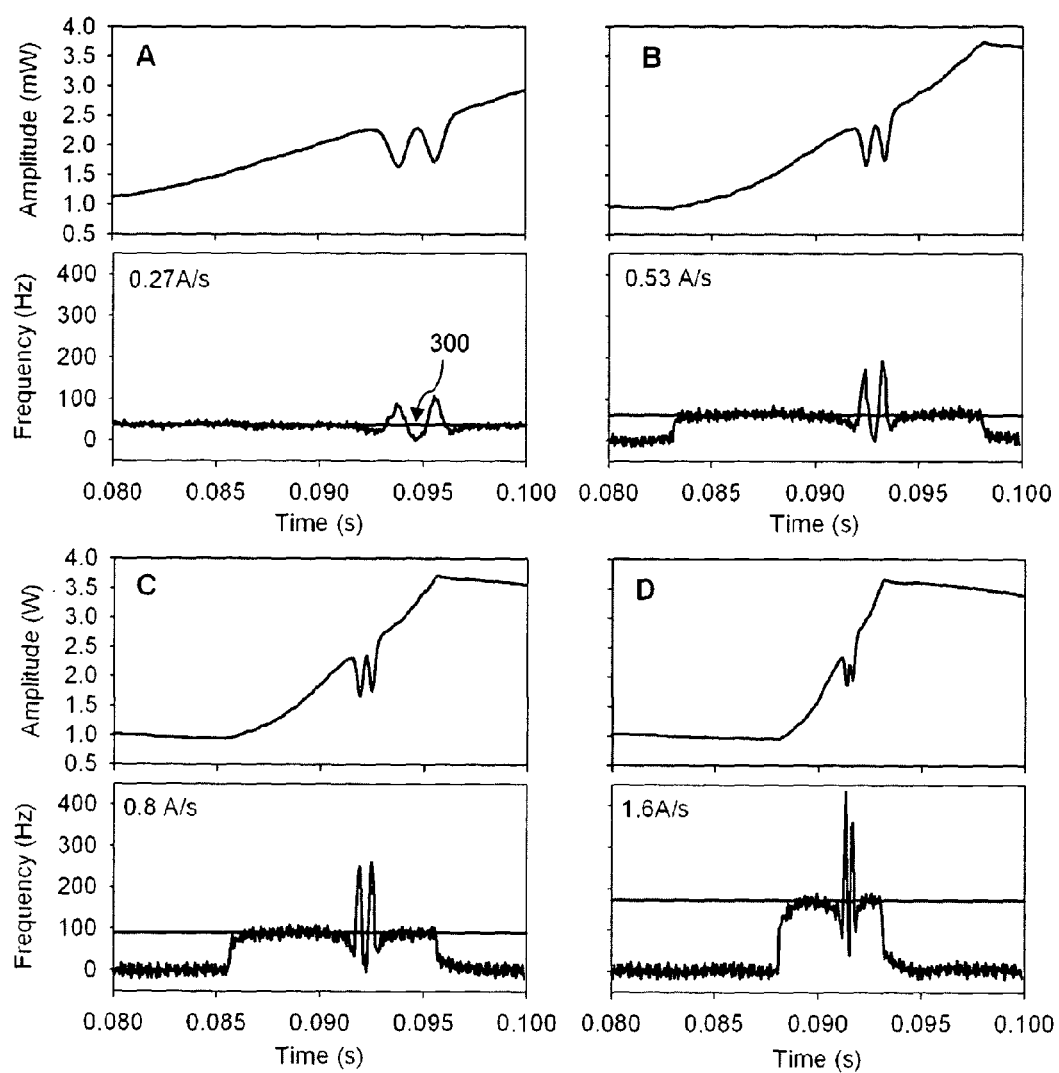
FIG. 4 shows graphical results obtained from the system of FIG. 1.

FIG. 4 shows absorption and demodulated frequency when measuring a NO doublet with a quasi-linear laser frequency scan at different scanning speeds. A: 173 Hz/ns, B: 347 Hz/ns, C: 521 Hz/ns, D: 1042 Hz/ns. The grey straight line 300 refers to the constant frequency value appearing in Equation 9.

Figure 5:
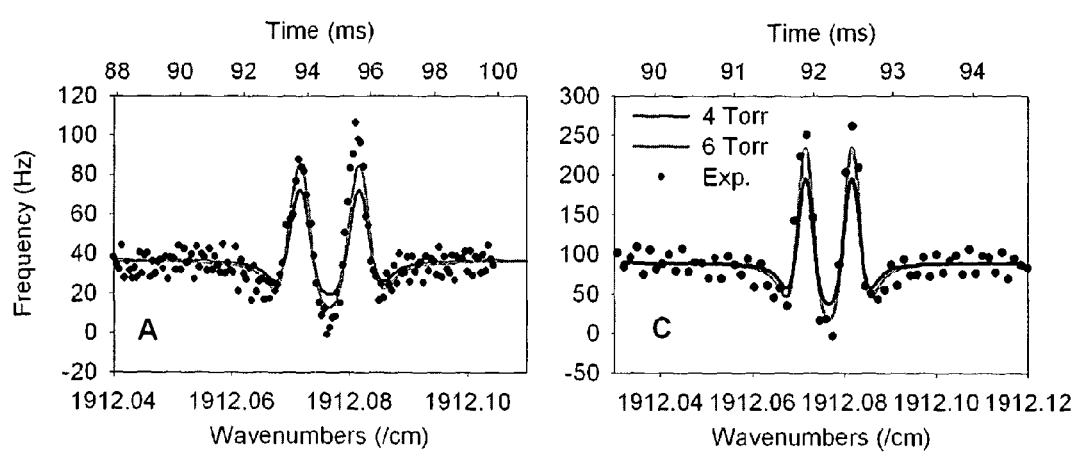
FIG. 5 shows further graphical results obtained from the system of FIG. 1.

The spectra shown in FIGS. 4A and 4C have been compared with the theoretical calculations based on the model presented above. FIG. 5 shows comparisons for two spectra (A and C) between experimental results and a model for the NO doublet at 1912.075 cm-1. Due to uncertainty in the total pressure, calculations for 4 and 6 Torr have both been made. The parameters used to generate the calculated spectra are provided in table 2. Apart from a slight under sampling in the case of spectrum C, the agreement is shown to be very good.

TABLE 2

Parameters used for calculated spectra a appearing in FIG. 4.

| | |
|---|---|
| Laser tuning rate | −21.74 cm⁻¹/A |
| Laser modulation p-p | 8 mA |
| Triangular waveform frequency | 100 (C) and 33 (A) Hz |
| Central wavenumber | 1912.075 cm⁻¹ |
| AOM frequency | 40 MHz |
| Air path difference ΔL | −8.61 cm (C) and |
| Cell length Lc | 15.0 cm |
| NO mixing ratio | 1% |
| Total pressure | 4 Torr and 6 Torr |

Measurements at High Laser Frequency Scanning Speed

As the frequency signal scales with the laser frequency tuning speed, spectral tuning capabilities of the QCL 20 may be exploited. In this example, the modulation bandwidth of the current source (250 kHz) and the acquisition bandwidth of a spectrum analyzer (not shown in the figures) performing the frequency demodulation (110 MHz) are the two main limitations that may prevent signals being acquired at very high laser frequency scan speed.

Figure 6:
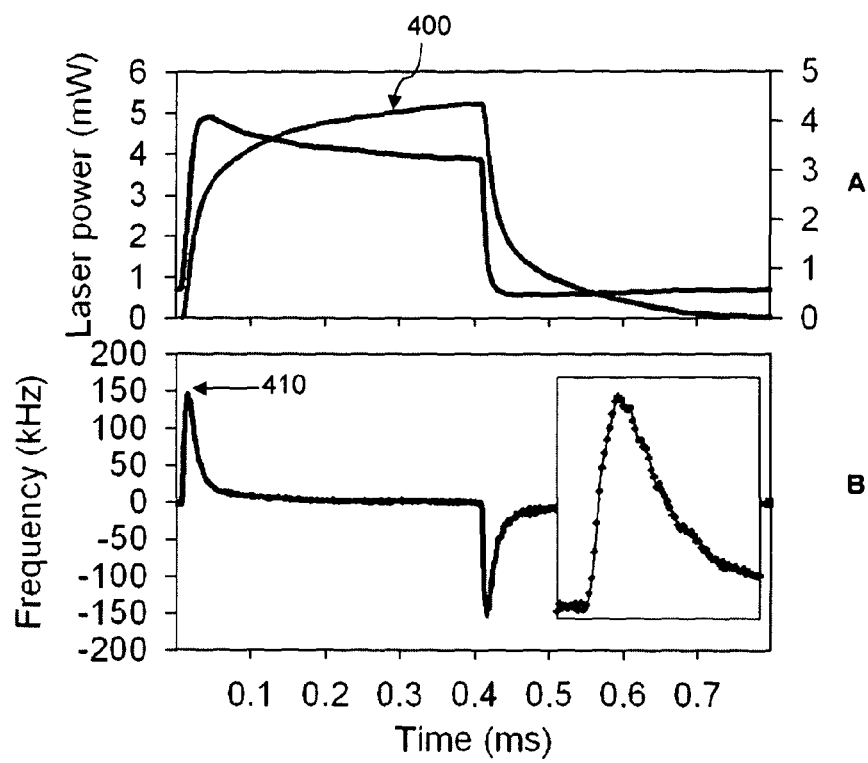
FIG. 6 shows further graphical results obtained from the system of FIG. 1.
Figure 7:
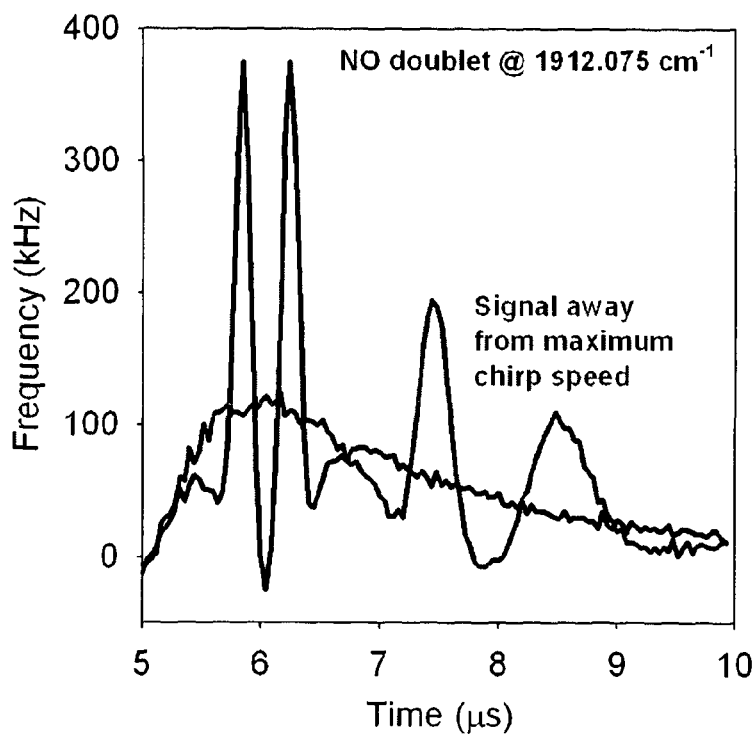
FIG. 7 shows further graphical results obtained from the system of FIG. 1.

A current step of few tens of mA may be applied to the QCL 20, for instance. With the sample cell 70 removed from the optical path, the frequency demodulated signal is:

$$2\pi \cdot f(t) = \frac{\Delta L}{c} \cdot \frac{d\omega}{dt}, \quad \text{(Equation 17)}$$

and therefore may provide information on the evolution of the laser frequency while the current step is applied. FIG. 6 shows a graphical representation of the laser power (A), the demodulated frequency signal (B), and the corresponding laser frequency evolution when applying an 8 mA (example) amplitude square wave at 1 kHz. The demodulated frequency plot (B) indicates that during the current step, the laser frequency tuning speed increases, then reaches a maximum (localized linear chirp), and decreases. According to (Equation 17), the integral of this signal gives the evolution of the laser frequency with time during the scan. This integral has been calculated and is shown as line 400 in FIG. 6. The optimum region to perform measurements may be where the tuning speed is maximum, which means at the top of the peak 410 in the frequency record. FIGS. 6 and 7 show the evolution of laser power and laser chirp rate during a square waveform current modulation. This effect can be seen more clearly on the FIG. 7 (10 scans averaged). By adjusting the QCL DC current, the NO doublet may be located where the laser tuning speed is maximum and subsequently away from that position. The effect on the signal amplitude is therefore detectable.

In this example, varying the amplitude of the current step modifies the laser frequency scan speed: 16 mA gives a peak at 766 kHz and 24 mA gives 1055 kHz, corresponding respectively to 2.7 MHz/ns and 3.7 MHz/ns given the 8.61 cm optical path difference.

With the same type of laser current modulation (16 mA current step), the sample cell 70' is placed in position 2 (cf. FIG. 1). The corresponding spectra are shown in FIG. 8, along with calculated spectra using the model described above.

Figure 8:
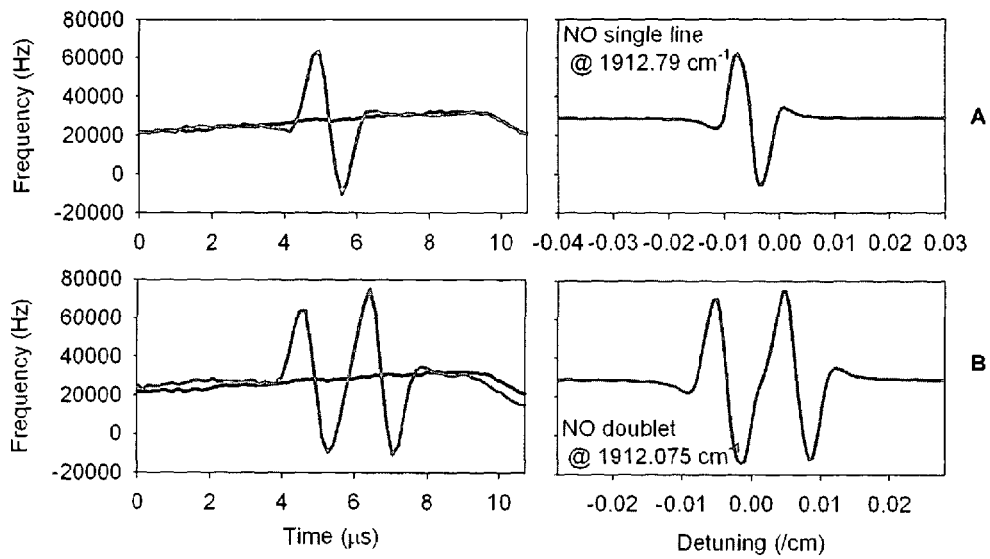
FIG. 8 shows further graphical results obtained from the system of FIG. 1.

In particular, FIG. 8 shows spectra recorded with the sample cell 70' in position 2 for the non-resolved doublet (upper plots A) and the doublet (lower plots B). The current step may be 16 mA, applied at a 100 kHz frequency. The plots on the left hand side of FIG. 8 are actual results and the plots on the right hand side are corresponding calculated spectra.

The calculated spectra are in good agreement with the experimental or actual data. However, calculations have been made assuming a laser linear frequency chirp. The slope in the experimental spectra baseline indicates some non-linearity in the actual laser frequency chirp.

The approach provides at least three advantages:

Possibility to suppress a baseline of DC offset: With the sample cell 70, 70' either in position 1 or 2, two optical arms may be balanced so that the measured signal is substantially zero when no refractive index change occurs. In tunable laser absorption spectroscopy, the signal to be measured is power-changed over a baseline, which may be several order of magnitude greater than the signal itself. This may be avoided and a fuller dynamic range and resolution of acquisition system may be used with the present described system.

Measurement of a pure frequency signal: the information may be modulated in frequency, and frequency signals may be measured with very higher accuracy. The approach is therefore more immune to laser power variation, or intensity noise. The contrast of the frequency signal due to refractive index change may be measured for different laser powers. This contrast may be calculated by taking the widest extend on the frequency signal (from min to max) divided by peak-to-peak noise amplitude in the frequency signal. Table 3 shows measurements of the frequency signal contrast as the laser power is varied over five orders of magnitude. It appears that despite a variation of five orders of magnitude in the laser power, the frequency signal remains mostly unaffected.

| | Beating signal power (μW) | | | |
|---|---|---|---|---|
| | 0.1 | 10 | 100 | 1000 |
| Frequency signal contrast | 9.5 | 15 | 11.2 | 20.2 |

Scaling of the signal amplitude with the laser frequency scanning speed: this advantage is particularly relevant to the use of QCL (but can be seen in other laser sources), which are solid-state lasers that can be chirped at high speed. Frequency scanning speed up ~260 MHz/ns may be observed. An intra-pulse scanning method may generate higher chirp rates and therefore may be used with improved results.

Comparison Between the Two Cell Positions

With the sample cell 70 in position 1 (see FIG. 1), where only one beam passes through the sample cell 70, the frequency-demodulated signal 90 contains information of the first derivative of the refractive index. In this configuration, substantially perfect optical path balancing may be difficult for longer paths. For instance with a long multi-pass cell it may become impractical.

This configuration is particularly suited to laser chirping with a highly linear rate. In this case, the AOM 30 may not be needed as the carrier frequency may originate directly from a fixed frequency term due to the path difference between the two beams. However, the level of chirp rate stability required not to interfere with refractive index change signals is high, and preferably should be below the frequency accuracy of the demodulation system 91, 92.

In the alternate configuration, the sample cell 70' being in position 2 (as depicted in FIG. 1), balancing to obtain a zero baseline may be more easily be achieved. In this situation, under the approximation of (Equation 12), the information measured may be proportional to the second derivative of the refractive index. However, for spectral features linewidth comparable to the AOM frequency, an additional optimization may be performed where a factor two increase (approximately) in the signal amplitude may be achieved compared to the sample cell 70 in position 1.

Detection Limits

Figure 9:
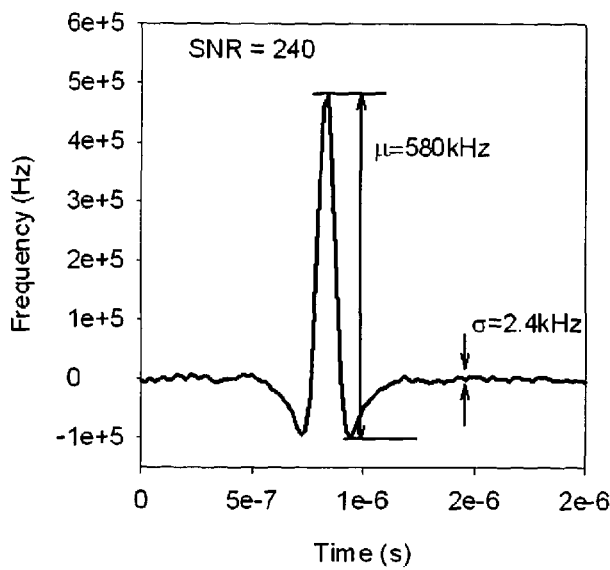
FIG. 9 shows further graphical results obtained from the system of FIG. 1.

A first hint on the detection limit capabilities on the refractive index change can be investigated on the experimental NO spectra. In this example, the laser was excited by a 14 mA current step and was centred on the single NO line at 1912.79 $cm^{-1}$, so that the transition centre frequency corresponds to a maximum laser frequency tuning speed. The baseline was corrected with a polynomial of the third order and 100 single scans were averaged. The corresponding recorded signal is given in FIG. 9. FIG. 9 shows NO transition at 1912.79 cm-1 during a 14 mA laser step. 100 scans were averaged and the baseline was corrected by a third order polynomial. The signal-to-noise ratio may be calculated by dividing the peak-to-peak amplitude of the signal with the standard deviation observed on the baseline and was found to be 240 in this example.

This signal was obtained for a 1% NO concentration, a path length of 15 cm and a total time of 200 µs. From these data, a detection limit (SNR=1) of 0.9 ppm for 1 meter path length and 1 s integration time may be extrapolated. Providing that the noise remains the same at very high scan speed, for a laser chirp rate of 300 MHz/ns, at least two orders of magnitude may be gained on the detection limit.

In this approach it may be shown that the refractive index change signal scales with the laser chirp rate for certain configurations. This feature makes the method particularly relevant to QCL spectroscopy, as very high chirp rate may be obtained.

Nitric Oxide diluted in dry nitrogen has been used as a test sample in this example. A detection limit of at least 0.9 ppm for 1 m path length and is integration time has been extrapolated from the experimental spectra. Two order of magnitude improvements are expected when operating QCLs at their highest chirp rate.

Implementing a system to benefit from the highest QCL chirp rates may provide further advantages, involving the implementation of an ad hoc and high speed frequency demodulation apparatus. The tailoring of laser injection current waveform taking into account the QCL thermal response may also be advantageous.

Figure 2:
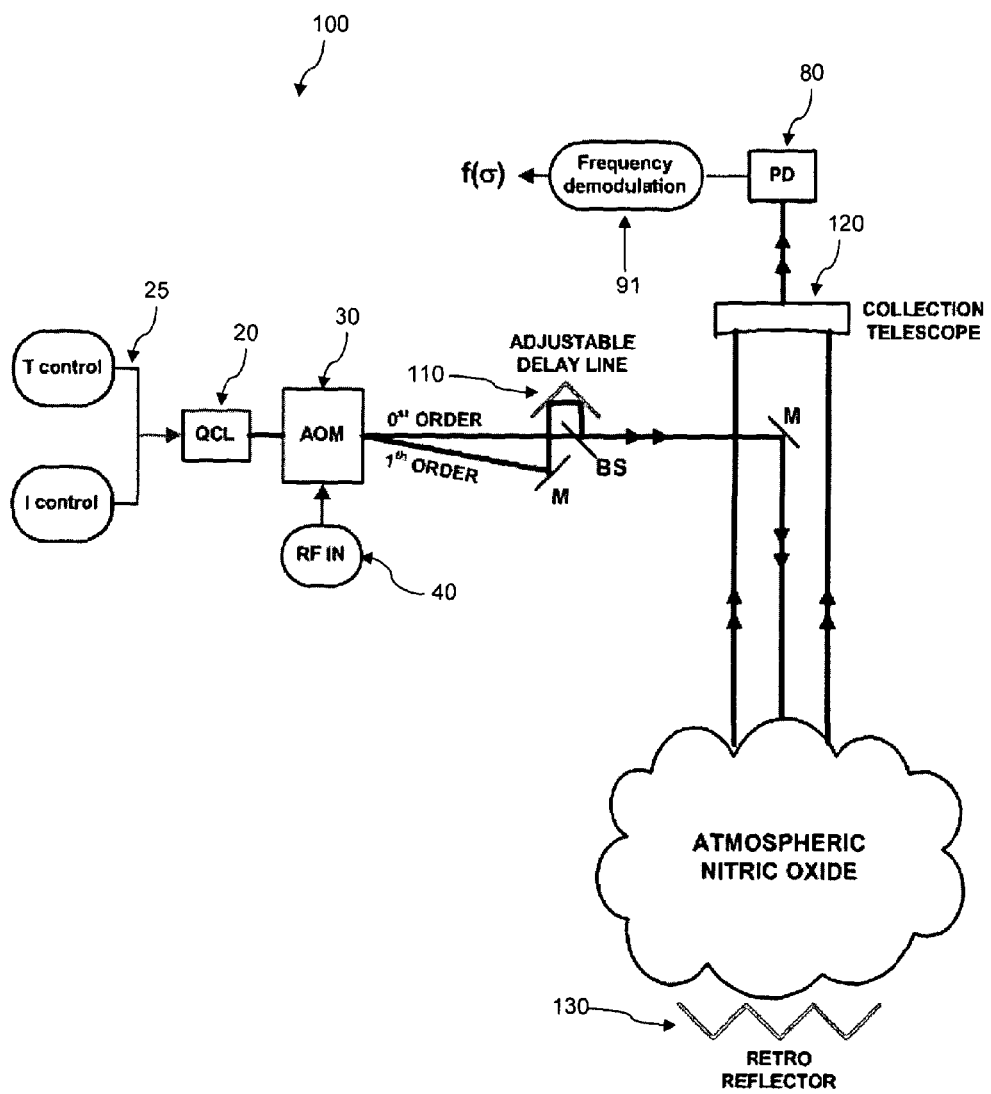
FIG. 2 shows a schematic diagram of an alternative system for detecting a species in the atmosphere.

FIG. 2 shows a schematic diagram of a further example system 100 for use in open path monitoring. In a particular and more specific example, this may be open-path monitoring of nitric oxide (NO) in the atmosphere. NO is a very important pollutant mainly stemming from combustion reactions and involved in urban ozone pollution and smog formation. Typical concentration of NO in the atmosphere varies from 10 ppb (unpolluted) to 200 ppb (polluted). A monitoring system may then be as depicted in FIG. 2 with features similar to those of FIG. 1 having the same reference numerals. In this example, the two combined beams are directed towards a distant retroreflector 130, typically a few hundreds of meters away from the emitting system.

The laser may also be a QCL 20 emitting in the 5.2 µm range, targeting a NO ro-vibrational transition from the fundamental band.

A delay line 110 may be introduced into the setup to balance the two beams paths, thus suppressing an offset in the measured frequency signal. The measured signal may also have at least some immunity to power amplitude variations. A few microsecond duration of the laser chirp reduces the effect of atmospheric turbulences.

The retro-reflected light may be collected by a telescope 120 and directed onto the photo detector 80.

With this example system 100, based on an extrapolation of results, a NO detection level may be calculated to be in the range of 10 ppb. The experimental conditions may for instance, be:

laser chirp speed: 300 MHz/ns
  200 µs integration time
  100 m open path
or other suitable values.

In a further example, explosives may be detected. For instance, ammonium nitrate $NH_4NO_3$ is an oxidizing agent used in improvised explosive devices and may be detected in the atmosphere by the apparatus shown in FIG. 2. In this case, decomposition into $NH_3$—$HNO_3$—$N_2O$ occurs and the antisymmetric stretch of the group $NO_2$ 1560 $cm^{-1}$ may be detected as the detected spectral feature.

Figure 3:
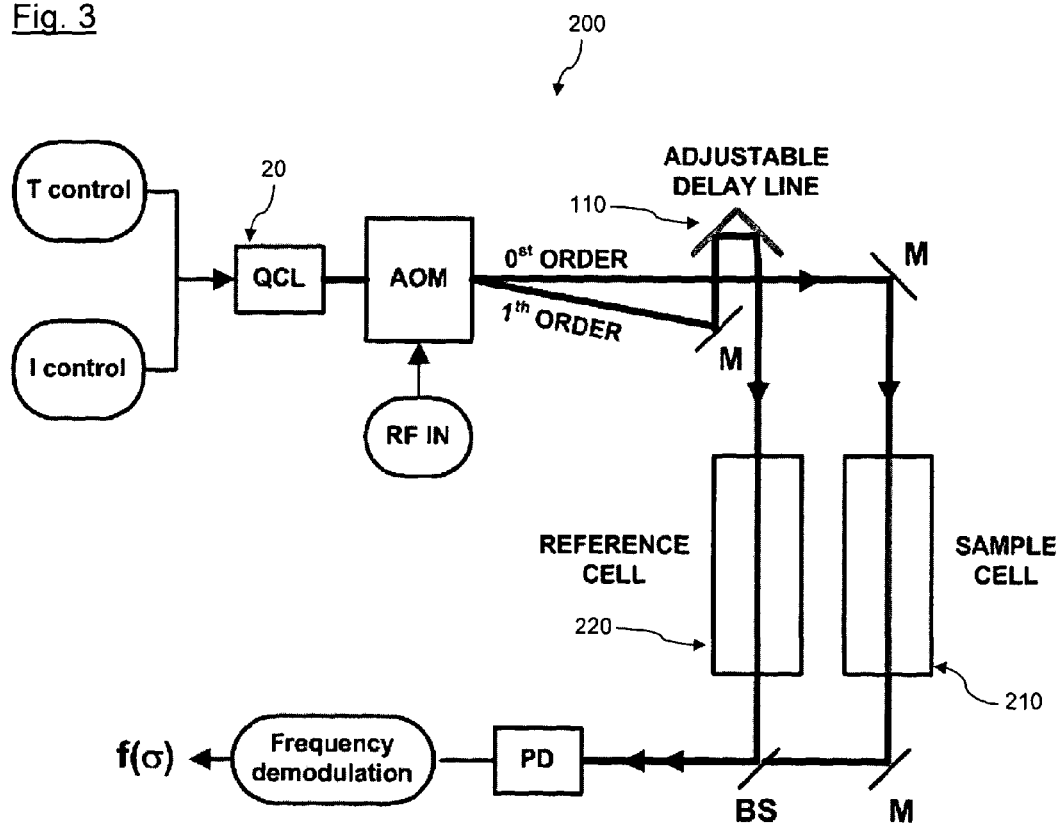
FIG. 3 shows a schematic diagram of a further alternative system for detecting a species in a dilute medium including a reference cell and a sample cell.

FIG. 3 shows a schematic diagram of a further example system 200. This example arrangement may be used for in situ, real time, referenced chemical sensing and concentration measurements. In this example, the two beams do not travel together through a sample medium but instead go through two preferably identical cells. A sample cell 210 may contain an unknown sample, for instance. A reference cell 220 may contain a reference mixture, for example. The system 200 also accommodates an adjustable delay line 110 to balance the two beams.

As an example we may measure the isotopomer $^{13}CO_2$ in air at 4.3 µm, using the QCL 20. Measuring in-situ, real time, isotopomer concentrations has many applications in atmospheric process studies, geochemistry, oil and gas prospection, counterfeited products detection, medical studies, for example.

The reference cell may contain a calibrated mixture of $^{13}CO_2$ in synthetic air. In the sample cell 210, ambient air may flow. Preferably, the reference mixture and the sample need to be kept at the same pressure. Other calibrated mixtures may be used.

In this example, the signal amplitude obtained after frequency demodulation may provide information on the difference of $^{13}CO_2$ concentration between the sample and the calibrated mixture. If we assume that ambient air is being monitored, the $CO_2$ concentration may be 380 ppm. Targeting the $^{13}CO_2$ line at 2298.5 $cm^{-1}$ (4.35 µm), for a 1 meter path length, and 1 second integration time then a 90 ppb $^{13}CO_2$ concentration change may at least be detected.

As will be appreciated by the skilled person, details of the above embodiment may be varied without departing from the scope of the present invention, as defined by the appended claims.

For example, different lasers or laser wavelengths may be used. Species other than molecules may be detected including atomic samples and plasmas. Samples in the liquid and solid phase may also be used. The $0^{th}$ beam or the $1^{st}$ order beam (or both) from the AOM may pass through the sample cell 70, 70'.

Many combinations, modifications, or alterations to the features of the above embodiments will be readily apparent to the skilled person and are intended to form part of the invention.

The invention claimed is:

1. A method of detecting a species in a dilute medium comprising:
    providing a first laser beam and a second laser beam coherent with each other, and having a matching chirp pattern;
    passing at least the first laser beam through the dilute medium, whilst the chirp pattern of the first laser beam crosses at least a part of a spectral feature of the species;
    mixing the first and the second laser beams to form a mixed beam;
    detecting the mixed beam to form an output signal during the chirp pattern;
    processing the output signal to measure changes in the mixed beam caused by refractive index variations in the dilute medium across the spectral feature;
    determining a measure of the species from the changes in the measured properties; and
    the method further comprising applying an optical frequency shift to the first or second laser beam before mixing the first and the second laser beams.

2. The method of claim 1, wherein the first and second laser beams both pass through the dilute medium.

3. The method of claim 2, wherein the chirp pattern of the second laser beam does not cross the spectral feature of the species.

4. The method of claim 2 or claim 3, wherein the measured changes in the mixed beam include changes in an optical frequency difference between the first and second laser beams.

5. The method according to claim 2, wherein an optical frequency difference is between 1 MHz and 1 GHz.

6. The method according to claim 2, wherein the detecting step further comprises detecting a beat signal in the mixed beam due to an optical frequency difference.

7. The method of claim 6, wherein the changes in the mixed beam caused by the refractive index variations includes changes in phase and the processing step further comprises measuring the changes in phase of the mixed beam.

8. The method of claim 6, wherein the detecting step further comprises detecting the frequency changes in the beat signal.

9. The method of claim 1, wherein processing the output signal further comprises measuring a change in optical path difference between the first laser beam and the second laser beam caused by refractive index variations in the dilute medium across the spectral feature.

10. The method of claim 9, wherein the change in optical path difference is measured by comparing phase properties of the mixed beam.

11. The method according to claim 1, wherein the first and second laser beams are generated using a quantum cascade laser.

12. The method according to claim 1, wherein during the chirp pattern, the first and second laser beams change frequency at a rate of at least 100 Hz/ns, and more preferably at least 100 KHz/ns.

13. The method according to claim 1, wherein each chirp pattern crosses at least a part of the spectral feature in less than 10 msec, and more preferably in less than 10 μs.

14. The method according to claim 1, wherein the spectral feature is selected from the group consisting of: electronic absorption, molecular transition, rotational transition, ro-vibrational transition, band gap and vibrational band.

15. The method according to claim 1, wherein
    the dilute medium is a gas sample, and
    the method detects a species in the gas sample using changes in refractive index of the gas sample across at least part of a spectral feature of the species in the gas sample.

16. Apparatus for detecting a species in a dilute medium, the species having a spectral feature, the apparatus comprising:
    a beam source arranged to generate a first laser beam and a second laser beam coherent with each other, and having a matching chirp pattern;
    a beam guide arranged to pass at least the first laser beam through the dilute medium;
    a beam mixer arranged to mix the first and the second laser beams to form a mixed beam;
    a detector arranged to detect, during the chirp pattern, the mixed beam and to measure changes in the mixed beam caused by refractive index variations in the dilute medium across a spectral feature;
    an output providing a signal that changes in response to the measured changes; and
    the apparatus further comprising an optical frequency shifter arranged to apply an optical frequency shift to the first or second laser beam before the beam mixer mixes the first and the second laser beams.

17. The apparatus of claim 16, wherein the beam guide is further arranged to guide the first and second laser beams through the dilute medium.

18. The apparatus of claim 17, wherein the beam guide is further arranged to guide the first and second laser beams through an open atmosphere.

19. The apparatus of claim 17 or claim 18, wherein the optical frequency shifter is an acousto-optic modulator, AOM.

20. The apparatus according to claim 16, wherein the beam source is a quantum cascade laser, QCL.

21. The apparatus according to claim 16, wherein the beam source further comprises a laser driver arranged to provide a driving signal to produce the chirp pattern.

22. The apparatus according to claim 16 further comprising an adjustable delay line for changing the relative optical path lengths of the first and second laser beams.

23. The apparatus according to claim 16, wherein the detector is an optical heterodyne detector.

24. The apparatus according to claim 16, wherein the detector further comprises an amplitude demodulator and/or a frequency demodulator.

25. The apparatus according to claim 16, further comprising a cell for containing the dilute medium.

26. The apparatus of claim 25 further comprising a second cell for containing a reference sample, wherein the beam guide is further arranged to guide the second laser beam through the second cell.

* * * * *